United States Patent [19]

Regnier et al.

[11] Patent Number: 4,613,601
[45] Date of Patent: Sep. 23, 1986

[54] (1-BENZODIOXIN-6-YLMETHYL)-4-SUBSTITUTED PIPERAZINES HAVING ANTIPSYCHOTIC ACTIVITY

[75] Inventors: Gilbert Regnier, Chatenay-Malabry; Jean-Claude Poignant, Bures sur Yvette, both of France

[73] Assignee: Adir, S.A.R.L., Neuilly-sur-Seine, France

[21] Appl. No.: 693,278

[22] Filed: Jan. 22, 1985

Related U.S. Application Data

[63] Continuation-in-part of Ser. No. 459,256, Jan. 19, 1983, abandoned.

[30] Foreign Application Priority Data

Jan. 21, 1982 [FR] France .................. 82 00870

[51] Int. Cl.[4] .................. C07D 401/04; C07D 403/04; A61K 31/495; A61K 31/505
[52] U.S. Cl. .................. 514/252; 544/295; 544/360; 544/366; 544/367; 514/253; 514/275
[58] Field of Search ............ 544/295, 360, 366, 367; 424/250, 251; 514/253, 275, 252

[56] References Cited

U.S. PATENT DOCUMENTS

| | | | |
|---|---|---|---|
| 3,917,597 | 11/1975 | Regnier et al. | 544/295 |
| 3,944,551 | 3/1976 | Reginer et al. | 544/295 |
| 4,112,092 | 9/1978 | Regnier et al. | 544/367 |
| 4,177,272 | 12/1979 | Regnier et al. | 544/366 |

Primary Examiner—George F. Lesmes
Assistant Examiner—S. A. Gibson
Attorney, Agent, or Firm—Gordon W. Hueschen

[57] ABSTRACT

Benzodioxine compounds of the formula:

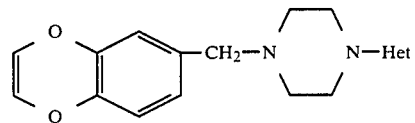

in which Het is a five- or six-membered heterocyclic radical containing from one to three hetero atoms, and from one to three double bonds, optionally substituted by one or more alkyl or alkoxy radicals each from $C_1$ to $C_5$.

These compounds and physiologically tolerable acid addition salts thereof may be used as medicines, especially in the treatment of psychoses.

5 Claims, No Drawings

(1-BENZODIOXIN-6-YLMETHYL)-4-SUBSTITUTED PIPERAZINES HAVING ANTIPSYCHOTIC ACTIVITY

This application is a continuation in part of Ser. No. 459,256 filed Jan. 19, 1983, now abandoned.

The present invention provides benzodioxine compounds of the formula:

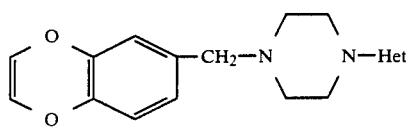

in which Het is selected from the group consisting of five- and six-membered heterocyclic radicals having from one to three hetero atoms such as oxygen, nitrogen and sulfur atoms, and containing from one to three double bonds, and these heterocyclic radicals mono- and poly-substituted by a radical selected from the group consisting of alkyl and alkoxy radicals, each having from one to five carbon atoms inclusive. As heterocyclic radicals there may be mentioned, for example, pyridyl, pyrimidinyl, pyrazinyl, thiazolyl, thiadiazolyl, oxadiazolyl and triazolyl radicals.

The present invention also provides acid addition salts of the compounds of the general formula I. The acid addition salts are preferably physiologically tolerable acid addition salts.

As a matter of fact, the compounds of the general formula I are weak bases which may be converted into acid addition salts by means of acids. As acids, which may be used for the formation of these salts there may be mentioned, for example, in the mineral series hydrochloric, hydrobromic, sulfuric and phosphoric acids, and in the organic series, acetic, propionic, maleic, fumaric, tartaric, citric, oxalic, benzoic, methanesulfonic and isethionic acids.

The Prior Art in this field may be illustrated by the U.S. Pat. No. 3,299,067 which provides as vasodilators, analgesics and anti-inflammatory agents, compounds of the general formula:

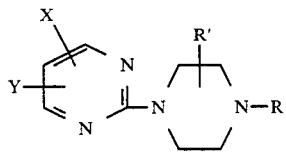

in which:
R may be, among others, a benzyl radical substituted on the phenyl ring by a —O—(CH$_2$)$_n$—O— group in which n is 1 or 2,
R' may be hydrogen, and
X and Y may be hydrogen, lower alkyl or lower alkoxy.

The Prior Art also includes the U.S. Pat. Nos. 3,917,597, 3,944,551, 4,112,092, and 4,177,272 each pertaining to 1,4-disubstituted piperazines showing CNS stimulation or stereotypy.

Among the compounds of the Prior Art, the most pharmacologically interesting one has the formula:

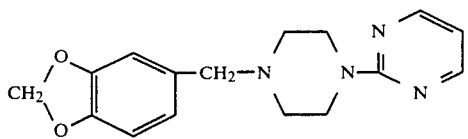

the international nonproprietary name of which is "Piribedil".

It was surprisingly found that the pharmacological behaviour of the compounds of the present invention is quite different from that of Piribedil.

The present invention further provides a process for preparing the compounds of the general formula I, which comprises:

either condensing a halo-compound of the general formula:

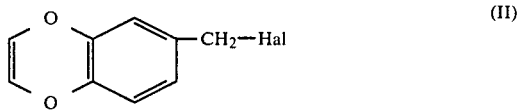

in which Hal is selected from the group consisting of a chlorine and a bromine atom, with a N-monosubstituted piperazine of the general formula:

in which Het has the meaning previously defined;

or condensing a halo-compound of the general formula:

in which Het and Hal have the meaings previously defined, with a N-monosubstituted piperazine of the formula:

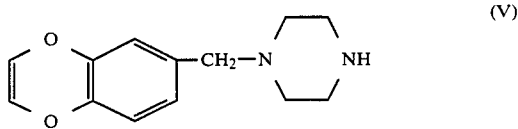

In these two cases, such a condensation is advantageously carried out in a polar solvent such as, for example, an alcohol having a high boiling point such as, for example, butanol or pentanol, or preferably an aliphatic amide such as, for example, dimethylformamide or dimethylacetamide, at a temperature within the range of 110° to 150° C. in the presence of an acceptor of the hydrohalic acid formed during the reaction. As acceptors, there may be mentioned, for example, alkali-metal or alkaline earth-metal salts of carbonic acid, such as, for example, sodium or potassium primary and secondary carbonates, calcium carbonate, or tertiary amines, such as, for example, triethylamine or pyridine. An excess of the N-monosubstituted piperazine of the formula III or V may also be used, the excess acting as the acid acceptor.

The present invention also provides a process for preparing the compounds of the general formula I, in which a mixture of an aldehyde of the formula:

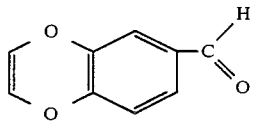 (VI)

and a N-monosubstituted piperazine of the general formula III, as previously defined, is submitted to a reductive alkylation, by means of cyano-borohydride of the formula BH₃CNM, in which M represents an alkali metal such as, for example, sodium or potassium.

This reductive alkylation is advantageously carried out according to the method of R. BORCH et al., J. Am. Chem. Soc. 93, 2897 (1971), at room temperature, by means of sodium cyano-borohydride, in the presence of hydrochloric or acetic acid, at a pH within the range of 6 to 8 in a suitable solvent such as, for example, tetrahydrofuran, dioxane, or an alcohol miscible with water, having a low molecular weight, such as, for example, methanol or ethanol.

The starting materials used in these processes are either known products, or compounds prepared according to methods described in the literature for preparing similar compounds, as mentioned in the following examples.

The compounds of the general formula I may be purified by physical methods such as, for example, distillation, crystallisation or chromatography, or by chemical methods, such as, for example, formation of addition salts, crystallisation of these salts and decomposition thereof by alkaline agents.

The compounds of the general formula I and physiologically tolerable salts thereof possess valuable pharmacological and therapeutic properties, especially psychotropic properties with a central dopaminergic mechanism. They may be used as medicines, especially in the treatment of psychotropic disorders in relation to a disturbance of the dopaminergic pathways, more particularly in the treatment of psychosis.

Their toxicity is low and their LD₅₀, determined in mice by intraperitoneal route, is higher than 300 mg/kg.

The central dopaminergic activity for the compounds of the present invention was determined, especially by measuring the rotations of the rat according to the method of Ungerstedt U., European Journal of Pharmacology, 5, (1968) 107–110. For the compounds of the present invention, administered at a dose of 25 mg/kg subcutaneously, up to 380 rotations were obtained in 45 minutes.

The present invention also provides pharmaceutical compositions comprising as active ingredient a compound of the formula I or a physiologically tolerable acid solution salt in admixture or conjunction with a pharmaceutically suitable carrier such as, for example, distilled water, glucose, lactose, starch, talc, ethylcellulose, magnesium stearate or cocoa butter.

The pharmaceutical compositions thus obtained are advantageously in unit dosage forms and may contain from 5 to 50 mg of active ingredient. They may be in the form of tablets, dragees, capsules, suppositories, injectable or drinkable solutions, and administered by oral, rectal or parenteral routes at doses within the range of 5 to 50 mg, once to thrice a day.

The following examples illustrate the invention, the melting points being determined in a capillary tube unless otherwise stated.

EXAMPLE 1

1-(benzodioxin-6-yl methyl)-4-(pyrimidin-2-yl)piperazine

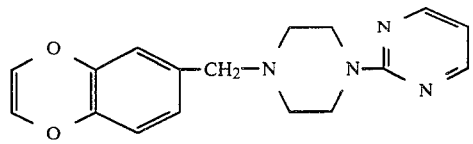

First method:

A solution of 24.5 g (0,134 mole) of 6-chloromethyl benzodioxine and 44 g (0.268 mole) of 1-(pyrimidin-2-yl)piperazine in 500 ml of xylene and 50 ml of dimethylformamide was refluxed for 3 hours. After completion of the reaction, the mixture was cooled, then taken off with 200 ml of water. The xylene layer was decanted off, then evaporated under reduced pressure. 37 g of an orange oil were obtained which was dissolved in 200 ml of anhydrous ethanol. After addition of an excess of hydrochloric acid ether solution the dihydrochloride crystallises. 39 g of 1-(benzodioxin-6-yl methyl)-4-(pyrimidin-2-yl)piperazine dihydrochloride white crystals were obtained with a melting point of 215°–220° C.

The starting 6-chloromethyl benzodioxin was prepared by chlorination in benzene, by means of SOCl₂, of 6-hydroxymethyl benzodioxine, M.P. 50° C., itself prepared by reduction with LiAlH₄ in tetrahydrofuran of 6-carbomethoxy benzodioxine, itself prepared according to G. COUDERT et al., Tetrahedron Letters 1978, 1059–1062.

Second method:

A solution of 11.4 g (0.1 mole) of 2-chloropyrimidine and 23.2 g (0.1 mole) of 1-(6-benzodioxinyl methyl)piperazine (oil) in 500 ml of pentanol, as refluxed for 6 hours, in the presence of 13.8 g (0.1 mole) of potassium carbonate. After the completion of the reaction, the so-formed salt was filtered off and the solvent was evaporated under reduced pressure. The so-obtained oily residue (30 g) was dissolved in 160 ml of anhydrous ethanol. After addition of an excess of hydrochloric acid ether solution, the dihydrochloride crystallises. 30 g of 1-(benzodioxin-6-yl methyl)-4-(pyrimidin-2-yl)piperazine dihydrochloride white crystals were finally obtained, melting at 215°–220° C.

The starting 1-(benzodioxin-6-yl methyl)piperazine was prepared by heating 6-chloromethylbenzodioxine in butanol with an excess of anhydrous piperazine.

Third method:

To a solution of 8.1 g (0.05 mole) of 6-formylbenzodioxine (prepared according to G. COUDERT et al., Tetrahedron Letters 1978, 1059–1062) and 8.2 g (0.05 mole) of 1-(pyrimidin-2-yl)piperazine in a mixture of 50 ml of tetrahydrofuran and 50 ml of methanol, there were added 3.1 g (0.05 mole) of sodium cyano-borohydride and 10 ml of a 5N hydrochloric acid methanol solution. The stirring was maintained for two hours at room temperature, then the mixture was acidified until pH 1 with a 2N hydrochloric acid solution. The solvent was then evaporated under reduced pressure. The residue was taken off with 50 ml of water, extracted with ether and alkalised with an excess of potassium carbonate. The base was finally extracted with chloroform. After treatment with an excess of hydrochloric acid ether solution the dihydrochloride crystallises. 7 g of 1-(benzodioxin-6-yl methyl)-4-pyrimidin-2-yl)piperazine dihydrochloride, white crystals were finally obtained, melting at 215°-220° C.

EXAMPLES 2 TO 9

The following compounds were prepared according to the methods given in Example 1:

2. 1-(benzodioxin-6-yl methyl)-4-(2-pyridyl)piperazine, M.P. of its dihydrochloride >250° C. with decomposition (anhydrous methanol), starting from:
   6-chloromethyl benzodioxine and 1-(2-pyridyl)piperazine, or
   2-chloropyridine and 1-(benzodioxin-6-yl)methyl)piperazine, or
   6-formylbenzodioxine and 1-(2-pyridyl)piperazine.

3. 1-(benzodioxin-6-yl methyl)-4-(1,3-thiazol-2-yl)piperazine, M.P. of its dihydrochloride dihydrate >220° C. (anhydrous methanol), starting from:
   6-chloromethyl benzodioxine and 1-(1,3-thiazol-2-yl)piperazine, or
   2-chloro 1,3-thiazole and 1-(benzodioxin-6-yl methyl)piperazine, or
   6-formyl benzodioxine and 1-(1,3-thiazol-2-yl)piperazine.

4. 1-(benzodioxin-6-yl methyl)-4-(1,3,4-thiadiazol-2-yl)piperazine, M.P. of its dihydrochloride >250° C. with decomposition, (anhydrous ethanol), starting from:
   6-chloromethyl benzodioxine and 1-(1,3,4-thiadiazol-2-yl)piperazine, or
   2-chloro 1,3,4-thiadiazole and 1-(benzodioxin-6-yl methyl)piperazine, or
   6-formyl benzodioxine and 1-(1,3,4-thiadiazol-2-yl)piperazine.

5. 1-(benzodioxin-6-yl methyl)-4-(pyrazin-2-yl)piperazine, M.P. of its dihydrochloride >258° C. with decomposition (anhydrous ethanol), starting from:
   6-chloromethyl benzodioxine and 1-(pyrazin-2-yl)piperazine, or
   2-chloropyrazine and 1-(benzodioxin-6-yl methyl)piperazine, or
   6-formyl benzodioxine and 1-(pyrazin-2-yl)piperazine.

6. 1-(benzodioxin-6-yl methyl)-4-(4-methyl-2-pyridyl)piperazine, starting from:
   6-chloromethyl benzodioxine and 1-(4-methyl-2-pyridyl)piperazine, or
   4-methyl-2-chloro pyridine and 1-(benzodioxin-6-yl methyl)piperazine, or
   6-formyl benzodioxine and 1-(4-methyl-2-pyridyl)piperazine.

7. 1-(benzodioxin-6-yl methyl)-4-(6-methoxy-2-pyridyl)piperazine, starting from:
   6-chloromethyl benzodioxine and 1-(6-methoxy-2-pyridyl)piperazine, or
   6-methoxy-2-chloro pyridine and 1-(benzodioxin-6-yl methyl)piperazine, or
   6-formyl benzodioxine and 1-(6-methoxy-2-pyridyl)piperazine.

8. 1-(benzodioxin-6-yl methyl)-4-(1,2,4-oxadiazol-5-yl)piperazine, starting from:
   6-chloromethyl benzodioxine and 1-(1,2,4-oxadiazol-5-yl)piperazine, or
   5-chloro 1,2,4-oxadiazole and 1-(benzodioxin-6-yl methyl)piperazine, or
   6-formyl benzodioxine and 1-(1,2,4-oxadiazol-5-yl)piperazine.

9. 1-(benzodioxin-6-yl methyl)-4-(4-methyl 1,2,4-triazol-3-yl)piperazine, starting from:
   6-chloromethyl benzodioxine and 1-(4-methyl 1,2,4-triazol-3-yl)piperazine, or
   3-chloro-4-methyl 1,2,4-triazole and 1-(benzodioxin-6-yl methyl)piperazine, or
   6-formyl benzodioxine and 1-(4-methyl 1,2,4-triazol-3-yl)piperazine.

EXAMPLE 10

Pharmacological study of 1-(benzodioxin-6-yl methyl)-4-(pyrimidin-2-yl)piperazine (compound of Example 1)

As an example, a detailed pharmacological study was carried out using the compound of Example 1 of the present application.

The motor depressant effects of the compound of Example 1 have been studied in mice. Thus, it has been established that the compound of Example 1 provokes in mice a hypokinesia at all the doses studied from 20 to 160 mg/kg I.P. The compound of Example 1 produces the central depressant effects observed in the electro-encephalogram in rats. It causes an increase in total sleep (slow sleep and paradoxal sleep) at a dose of 30 mg/kg I.P. An increase of 100% is noted during the second hour following administration of the compound.

Piribedil, on the other hand, administered at the same dose, has a completely opposite effect on the E.E.G. (reduction of total sleep by 50%).

The effect of hypokinesia and that of sedation and central depression on the E.E.G. are the translation of an effect of the compound of Example 1 on the dopaminergic inhibitory auto-receptors situated in the brain of mice and rats. The compound of Example 1 induces practically no sterotypy in normal rats.

The research for stereotyped movements, proof of the existence of a direct post-synaptic dopaminergic stimulating activity, has been carried out in rats using the scale described by R. M. QUINTON and H. HALLIWELL, Nature, 200, 1963, 178–179. The experiment lasts 3 hours, the animals are observed every 30 minutes. The groups are made up of 8 rats each, and the results are the total scores of the accumulated individual scores of the stereotypies observed during the experiment (6 observations).

The compound of Example 1, at a dose of 80 mg/kg I.P. or S.C., induces very few stereotyped movements: the total score I.P. reached 52 in 3 hours. By subcutaneous administration, the score reached 49. Piribedil produces higher scores: 145 at a dose of 20 mg/kg I.P., 246 at a dose of 40 mg/kg I.P. These results show that the compound of Example 1 has no important stimulating activity on the dopaminergic post-synaptic receptors of the striatum in rats. On the other hand, Piribedil stimulates these receptors and therefore has a direct post-synaptic action.

Experiments have also been carried out on rats with unilateral lesions of the nigro-neostriatal tract.

These lesions are produced by local micro-injection of 6-hydroxy dopamine into the black substance of the rat, according to U. Ungerstedt; Europ. J. Pharmacol. 5, 1968, 107–110 and Advances in Neurology, vol. 3, Raven Press., New York (1973).

This treatment leads to a degeneration of the dopaminergic neurons coming from the nigra-substantia, going towards the neostriatum.

Furthermore, following this denervation, the post-synaptic receptors situated above the pithed tract, i.e., above the synapse which leads to the pithed neuron, become hypersensitive to the pharmacological dopaminergic agents administered. This direct activation of hypersensitive dopaminergic receptors then produces the supervention of a motor rotation behaviour in treated rats.

When the left nigro-striatal tract is destroyed, the rotations occur towards the right, on the opposite side to the lesion. The experimental groups each contain from 5 to 6 animals.

The compound of Example 1 provokes numerous rotations in the unilaterally pithed rat, on the right side, on the opposite side to the lesion.

For this compound, the average number of rotations in 45 minutes is:
  182 at a dose of 12.5 mg/kg S.C.;
  380 at a dose of 25 mg/kg S.C.;
  543 at a dose of 50 mg/kg P.O.

Piribedil provokes fewer of these rotations: 256 rotations on average over 45 minutes at a dose of 50 mg/kg P.O.

On this model alone, the compound of Example 1 acts as a direct stimulant on the hypersensitive post-synaptic dopaminergic receptors.

The direction of the rotations observed (towards the right) clearly indicates that this is a direct agonist type of activity. This is the only case where the compound of Example 1 can release a motor-stimulant activity, since the presynaptic inhibitory activity cannot exist (nigro-striatal tract destroyed), and that only the post-synaptic receptors remain, these being rendered hypersensitive to the agonist agent administered. This is the only case when a compound of Example 1 can act as a central stimulant by inducing rotatory movements on a pathological model.

On the other hand, in the normal animal, mice or rats, the compound of Example 1 only provokes an hypokinesia due to the preferential stimulation of the pre-synaptic dopaminergic receptors.

The anti-dopaminergic activity of the compound of Example 1 has been displayed by the experimental model of dopaminergic hyperactivity, i.e., that of mice submitted to d-amphetamine:

the administration of d-amphetamine, at a dose of 1 to 3 mg/kg I.P. in mice, releases the supervention of motor phenomena registered using an activograph.

The joint administration of the compound of Example 1 to mice submitted to d-amphetamine allows the observation of an inhibition of the motor phenomena due to the amphetamine.

As a matter of fact the doses of 20 or 40 mg/kg of the compound of Example 1 antagonise respectively the effects of 1 and 3 mg/kg I.P. of d-amphetamine.

d-amphetamine causes the liberation of dopamine at the cerebral level. This liberation induces a hypermotility and stereotyped movements of the head at strong doses. The amphetaminic psychosis exists in man and amphetamine is used to create psychosis models in animals cf. B. ANGRIST in "Stimulants", Raven Press, New York (1983). The compound of Example 1 diminishing the behavioural effects of amphetamine can thus be considered as an antipsychotic agent.

The anti-psychotic effect of the compound of Example 1 has also been displayed by the technique of active conditioning of the "shuttle box avoidance" type. The method used is based on the works of COURVOISIER et al., Arch. Int. Pharmacodyn. 92, 305–361, (1953), and of JANSSEN et al., Arzneim. Forsch. 15, 104–117, (1965).

The experiments are carried out on groups of 10 to 20 male WISTAR rats weighing between 300 g and 400 g. Each animal is submitted to two day-sessions per week, one after treatment carried out on the substance studied at a given dose, 30 minutes before the session, the other following the administration of a solute of NaCl (0.154M)—I.P. route in both cases. The compound of Example 1 has been administered in solution in sterile bi-distilled water, at doses of 6.25, 12.5, 25, 50 and 75 mg/kg. I.P.

Piribedil chosen as reference product has been administered at the same doses and by the same route. This method is used to show the anti-psychotic activity of a substance. It is known that anti-psychotic agents inhibit the conditioned shunning response, without modifying the escape response following an electric shock (Unconditioned response). The central depressors can jointly inhibit the conditioned response and the unconditioned response.

The results obtained are set out in the following table.

| | CONDITIONED AVOIDANCE RESPONSE INHIBITION IN THE RAT | | | | | | | |
|---|---|---|---|---|---|---|---|---|
| | Shunning response | | | Escape response | | | Crossings | |
| Treatment and dose mg/kg I.P. route | Number over 20 | % over 20 | % in relation to control animals | Number over 20 | % over 20 | % in relation to control animals | Number over 20 | % over 20 |
| NaCl controls (0.154 M) | 19.65 | 98.25 | | 0.35 | 1.75 | | 21.25 | |
| Compound of Ex. 1 | | | | | | | | |
| Compound of Ex. 1 6.25 | 19.7 | 98.5 | +0.25 | 0.30 | 1.5 | −14 | 20.6 | −3 |
| Compound of Ex. 1 12.50 | 19.4 | 97 | −1 | 0.6 | 3 | +71 | 18.0 | −15 |
| Compound of Ex. 1 25 | 19.4 | 97 | −1 | 0.6 | 3 | +71 | 19.2 | −9 |
| Compound of Ex. 1 50 | 16.8* | 84 | −15 | 3.2* | 16 | +814 | 22.9 | +8 |
| NaCl controls (0.154 M) | 19.7 | 98.5 | | 0.3 | 1.5 | | 15.6 | |
| Compound of Ex. 1 75 | 18.1* | 90.5 | −8 | 1.9* | 9.5 | +533 | 25.4* | +63 |
| NaCl controls (0.154 M) | 19.6 | 98 | | 0.4 | 2 | | 19.7 | |
| Piribedil 6.25 | 19.4 | 97 | −1 | 0.6 | 3 | +50 | 29.5* | +50 |
| Piribedil 12.50 | 19.1 | 98 | 0 | 0.4 | 2 | 0 | 28.9* | +47 |
| Piribedil 25 | 19 | 95 | −3 | 1 | 5 | +149 | 48.9* | +148 |

-continued

| Treatment and dose mg/kg I.P. route | CONDITIONED AVOIDANCE RESPONSE INHIBITION IN THE RAT | | | | | | | |
|---|---|---|---|---|---|---|---|---|
| | Shunning response | | | Escape response | | | Crossings | |
| | Number over 20 | % over 20 | % in relation to control animals | Number over 20 | % over 20 | % in relation to control animals | Number over 20 | % over 20 |
| Piribedil 50 | 19.4 | 97 | −1 | 0.6 | 3 | +50 | 42.9* | +118 |
| NaCl controls (0.154 M) | 19.7 | 98.5 | | 0.3 | 1.5 | | 15.6 | |
| Piribedil 75 | 17.8 | 89 | −10 | 2.2. | 11 | +633 | 33.5* | +115 |

NOTE = *STATISTICALLY SIGNIFICATIVE VARIATION P < 0.05

The compound of Example 1, at doses of 50 to 75 mg/kg I.P., diminishes the number of shunning responses respectively from 15 to 8%. The escape responses increase over the same period for the doses mentioned (from 800 to 500% respectively).

The compound of Example 1 therefore reduces the conditioned responses without diminishing the unconditioned escape responses. At a dose of 75 mg/kg I.P., the compound of Example 1 increases the number of spontaneous crossings by 63%. This implies that the compound of Example 1 has neither a mobility depressor effect, nor sedative effect, nor cataleptigenic effect. Piribedil, the reference dopaminergic agonist agent, has no agonistic effect on the shunning responses. On the other hand, at all the doses studied, 6.25 to 75 mg/kg I.P., Piribedil increases significantly the number of spontaneous crossings outside the shunning or escape response periods. These increases vary, according to the dose, from 50 to 150%. Thus the effects of Piribedil are different from those of the compound of Example 1, as there is no conditioning inhibitory phenomenon in the case of Piribedil, but only a motor stimulation, linked to the post-synaptic dopaminergic receptor stimulation effect occurring at the doses studied.

On the other hand, the results obtained with the compound of Example 1 for this test allow the conclusion that this compound has an anti-psychotic property, the effect observed being due to the inhibitory pre-synaptic dopaminergic auto-receptor stimulation.

The above results lead to the conclusion that the compound of Example 1 may be used in the treatment of schizophrenia or other psychoses.

We claim:

1. A compound selected from the group consisting of: benzodioxine compounds of the formula:

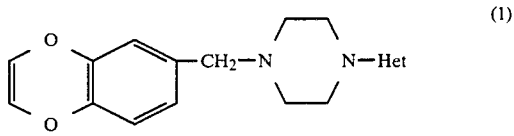

(1)

in which Het is a heterocyclic radical selected from the group consisting of pyrimidin-2-yl and 2-pyridyl; and physiologically tolerable addition salts thereof.

2. A compound of claim 1 which is 1-(benzodioxin-6-yl methyl)-4-(pyrimidin-2-yl)piperazine or its dihydrochloride.

3. A compound of claim 1 which is 1-(benzodioxin-6-yl methyl)-4-(2-pyridyl)piperazine.

4. A pharmaceutical compositions suitable for treating psychotic conditions containing as active ingredient an effective anti-psychotic amount of a compound of claim 1 together with a suitable pharmaceutical carrier.

5. A method for treating a living animal body afflicted with a psychosis, comprising the step of administering an amount of a compound of claim 1 which is effective for the alleviation of the said condition.

* * * * *